United States Patent [19]

Couse et al.

[11] 4,353,988

[45] Oct. 12, 1982

[54] GRID FOR USE IN COUNTING COLONIES OF BACTERIA PRESENT IN DISCRETE AREAS OF A SPIRAL DEPOSITION PATTERN

[76] Inventors: Nancy L. Couse, 2164 Zang St., Golden, Colo. 80401; Jeannette W. King, 2620 S. Race, Denver, Colo. 80210

[21] Appl. No.: 206,048

[22] Filed: Nov. 12, 1980

[51] Int. Cl.³ .............................................. C12M 1/00
[52] U.S. Cl. ..................................... 435/287; 435/30; 435/291; 435/292; 435/293; 435/297; 33/1 BB
[58] Field of Search ................. 435/30, 291, 297, 298, 435/292, 293, 808, 287, 317; 33/1 BB

[56] References Cited

U.S. PATENT DOCUMENTS

| | | | |
|---|---|---|---|
| 2,677,646 | 5/1954 | Lovell et al. | 435/297 X |
| 2,971,892 | 2/1961 | Carski | 435/298 |
| 3,065,150 | 11/1962 | Kravitz | 435/297 X |
| 3,203,870 | 8/1965 | Andelin | 435/298 |
| 3,630,849 | 12/1971 | Land et al. | 435/298 |
| 3,778,351 | 12/1973 | Roson | 435/30 X |
| 3,962,040 | 6/1976 | Campbell et al. | 435/30 X |
| 4,273,877 | 6/1981 | Anagnostopoulos | 435/293 |

*Primary Examiner*—Robert J. Warden
*Attorney, Agent, or Firm*—Edwin L. Spangler, Jr.

[57] ABSTRACT

This invention relates to an improved grid for use in counting the bacterial colonies present in defined areas of a spirally-deposited liquid sample containing steadily decreasing concentrations of a chemical to be tested, such grid being characterized by a transparent overlay upon which is imprinted a spiral defined by outlining the side margins of its convolutions while leaving the area therebetween blank, the spiral including at least two complete revolutions with common margins therebetween positioned to overlie the deposition spiral, the convolutions of the grid spiral being of constant width and not less than approximately three combined deposition spiral convolutions, the rate of divergence of the grid spiral convolutions being greater than those of the deposition spiral such that the former intersect the latter at least twice each revolution, and with at least a portion of the grid spiral being segmented to divide same into a plurality of discrete areas positioned to overlay areas of the deposition pattern containing different concentrations of the chemical. In one embodiment, the discrete areas are all located in a sector-shaped portion of the spiral defined by divergent radii; whereas, in another embodiment, all the discrete areas lie in end-to-end relation with all but the end one being of the same length.

15 Claims, 3 Drawing Figures

GRID FOR USE IN COUNTING COLONIES OF BACTERIA PRESENT IN DISCRETE AREAS OF A SPIRAL DEPOSITION PATTERN

Some years ago, the time-consuming and rather burdensome procedure of serially diluting bacteria was improved upon considerably by depositing the bacteria-laden liquid in a spiral pattern on the previously-plated agar surface of a single rotating culture dish. No useful purpose would be served by going into detail concerning this well-known technique or the method and apparatus used for making such depositions or counting the colonies of bacteria thus deposited since these matters are fully set forth in U.S. Pat. Nos. 3,799,844; 3,892,632; and 3,962,040, all of which have been assigned to the Department of Health Education and Welfare of the United States. For the present it should suffice to point out that the bacteria-laden liquid was laid down in the form of an Archimedes spiral upon the agar coating so as to effectively produce a continuous dilution thereof starting near the center with a high concentration and ending near the periphery of the dish with a low one.

In the testing for chemical mutagens to obtain a so-called "dose-response curve", the conventional practice used to be that of mixing sensitive bacteria with several different concentrations of chemical in a liquid and then plating each concentration on the agar surface of a separate culture dish. The several culture dishes were then incubated and the number of colonies on each plate counted. A direct correlation existed between the number of colonies present and the concentration of the chemical present which relationship forms the basis for the dose-response curve. More recently, this outdated procedure has been altered by spirally plating the test chemical using the above-mentioned apparatus and overlaying with sensitive bacteria. A complete dose-response relationship is obtained in one culture dish by so doing.

Now, in order for this spiral-deposition pattern to be quantitatively useful, some means must be provided for reading the number of colonies present in a given area. For instance, the number of colonies may be low at the beginning of the deposition because the high concentration of the chemical at this point may prove toxic to the bacteria. On the other hand, toward the end where the chemical concentration is dilute, this same diminution in colony count can occur, and oftentimes does, because the amount of chemical present is too small to be effective. In this situation, at some point in between the number of colonies reaches a maximum per unit area and this translates into the optimum chemical concentration.

So far as applicants are aware, only one so-called "counting grid" is available which, upon being placed beneath the completed spiral is effective to quantify the number of colonies present within a prescribed area thereof. This grid is marketed by Spiral Systems, Inc., of Bethesda, Md. and it consists of a circular, not a spiral, pattern divided into five major concentric rings. These rings are each then subdivided radially into a total of eight wedges or sectors.

In performing a standard assay using such a grid, the total volume of bacteria-laden liquid deposited in each of the discrete sectors is known, the several such sectors carrying distinctive number or letter designations. The number of colonies present in each of the several sectors is counted until a statistically significant number is found; whereupon, the concentration of cells in the original sample can be calculated based upon the known volume of bacteria-laden liquid present in the particular sector.

Using the foregoing technique for a standard assay, the starting and stopping points for the deposition are not important. Instead, the plate is placed randomly with respect to these counting sectors.

The provision of a dose-response curve, on the other hand, involves a more complex procedure for which the prior art concentric-circle grid proved to be unsatisfactory. When an attempt was made to count the colonies sequentially starting with the beginning of the spiral deposition pattern, the resulting counts exhibited periodicity rather than continuous change. More specifically, the counts within each ring showed regularly-occurring highs and lows as the number of cells within each wedge-shaped sector was counted using what is known in microbiological circles as the "Ames assay."

Part of the problem appeared to be caused by the fact that the prior art grid was circular and did not, therefore, follow the spiral deposition pattern along which the sample was laid down. Unfortunately, merely using a grid or template which did, in fact, follow the spiral deposition pattern also proved to be unsatisfactory for several reasons, the most significant of which is the fact that it proved to be impractical to count continuously along the exact deposition lines of the spiral. One reason for this is that the chemical diffuses into the convolutions of the spiral on either side thereof thus introducing inaccuracies in any count predicated upon the assumption that each such convolution remains separate and distinct.

While this diffusion problem was formidable in itself, even more so was that of overcoming the periodicity exhibited when the concentric circle grid was used. These problems along with that of determining the size, length and arrangement of counting segments which would produce a reliable cell count presented applicants with a severe challenge, one which they were fortunately able to solve by the simple yet unobvious expedient of first including within each segment of the counting grid, not one, but several deposition tracks. Next, while using a spiral grid, it proved to be necessary that it not follow the deposition spiral but instead intercept same at intervals selected to eliminate periodicity. Finally, not one but two different segment patterns have proven effective, the first consisting of a plurality of segments of different lengths depending upon their radial distance from the center and all lying within a common circular sector located opposite the point where the spiral deposition commenced and a second where all but the final segment have the same length measured along the grid spiral.

It is, therefore, the principal object of the present invention to provide a novel and improved spiral-patterned counting template for use in counting cell colonies produced in response to a chemical laid down in accordance with an Archimedes spiral.

A second object is the provision of a template of the type aforementioned which eliminates the problems associated with diffusion from one convolution of the deposition spiral to the next.

Another object of the invention herein disclosed and claimed is the provision of a segmented cell-counting grid which integrates with an Archimedes deposition spiral so as to eliminate periodicity.

Still another object of the within described invention is that of providing a novel spiral grid which is adaptable for use with automated counting procedures.

An additional objective is the provision of a device of the type aforementioned which is ideally suited for use in obtaining the data required for complete microbial dose-response curves in a single culture dish.

Further objects are to provide a spiral counting template which is simple, easy to use, versatile, inexpensive, reliable and fully compatible with existing spiral plating machines.

Other objects will be in part apparent and in part pointed out specifically hereinafter in connection with the description of the drawings that follows, and in which.

Figure 1:
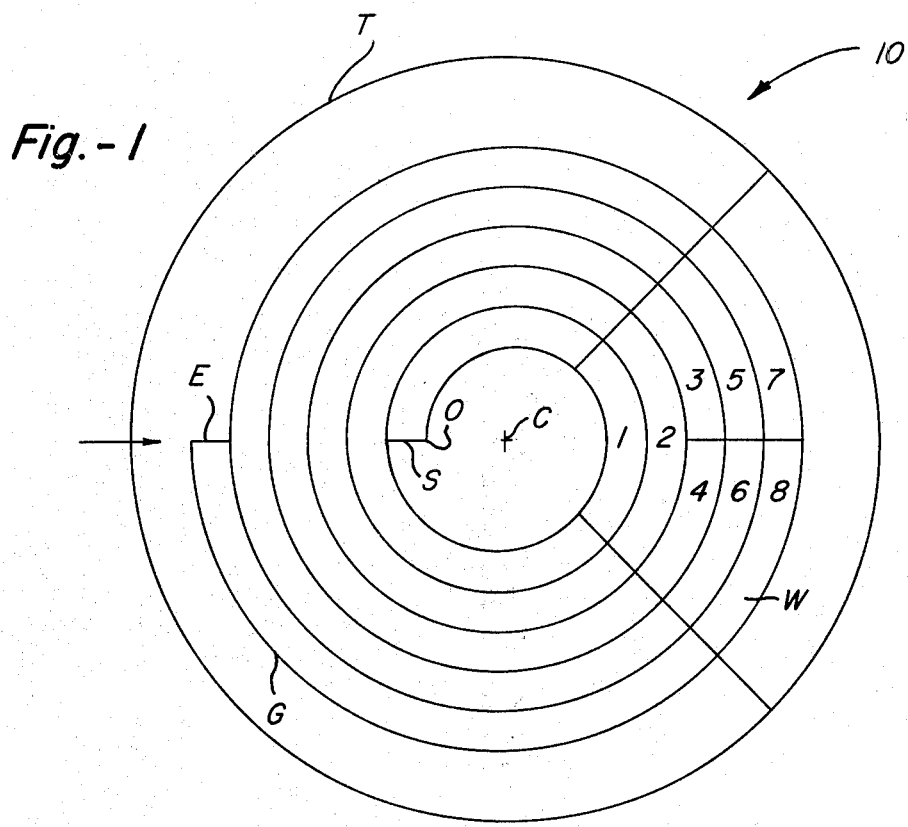
FIG. 1 is a plan view of a template having one form of the spiral counting grid of the present invention inscribed thereon.
Figure 2:
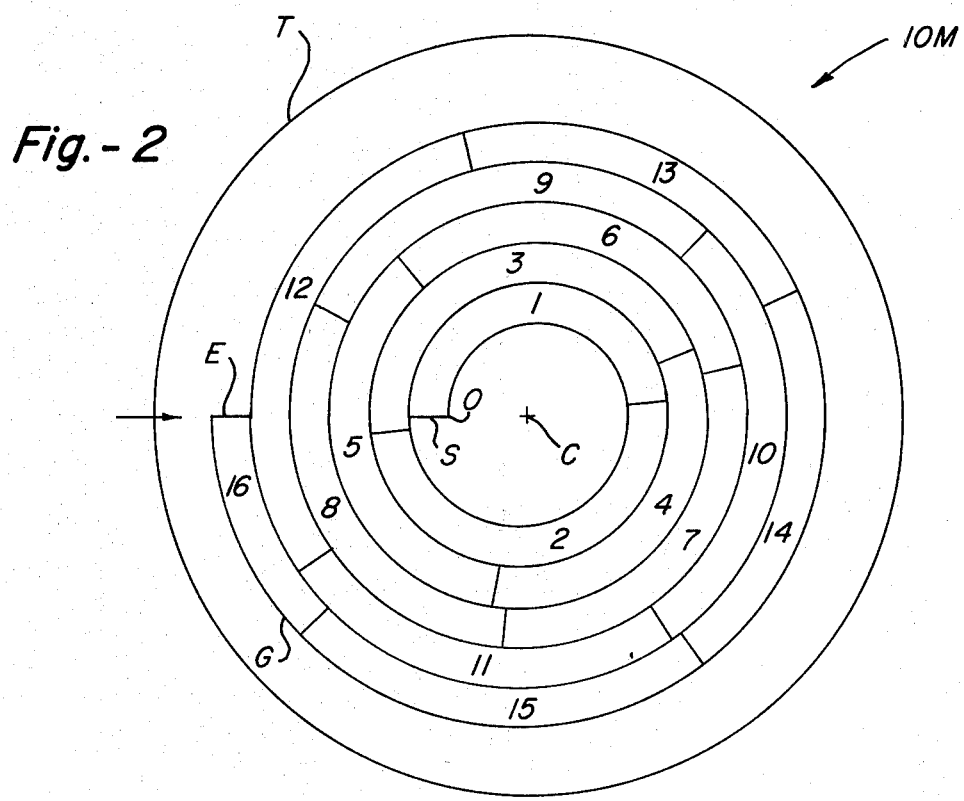
FIG. 2 is a plan view similar to FIG. 1 and to the same scale showing an alternate form of the grid using the identical spiral but different segmenting thereof; and, FIG. 3 is a diagram to a considerably larger scale showing only the central portion of the counting grid in relation to a corresponding portion of the spiral deposition pattern.

Referring next to the drawings for a detailed description of the present invention, both FIGS. 1 and 2 show a circular template T of transparent material having a spiral grid G inscribed thereon. The basic spiral grid G remains the same in both the FIG. 1 version which has been broadly designated by reference numeral 10 and in the alternate version thereof shown in FIG. 2 and which has been similarly identified by reference numeral 10M. Spiral grid G, in the particular form shown, consists of a total of five complete 360° convolutions beginning at starting point S adjacent the center C of the template and terminating at point E on the periphery thereof, point E being on the same radial line as starting point S. It can also be seen that the width of the five convolutions of the grid spiral remain constant from the beginning (S) to the end (E).

Next, while no attempt has been made to illustrate the entire deposition pattern D due to space limitations, enough thereof has been shown by way of phantom lines in FIG. 3 to which reference will now be made to delineate certain significant relationships between it and the counting grid G, the corresponding portion of which has been shown in full lines. It will be noted that deposition spiral D consists of a considerably tighter spiral than its counting grid counterpart G. Moreover, all of the convolutions of the deposition spiral, while also of a constant width, are considerably narrower than the convolutions of the grid spiral. More specifically, it has been found that the width of the counting grid spiral is advantageously selected such that it totals a whole number multiple greater than one of the width of the deposition spiral convolutions plus approximately one-half of such width. As illustrated, the selected whole number multiple is three which means that with the deposition spiral convolutions each having a width of 0.8 millimeters, the counting grid convolutions will each be 3.5×0.8 or 2.8 cm wide. Looking at this relationship somewhat differently, each counting grid convolution will preferably extend across a total of three deposition grid spiral convolutions and half way across the fourth. It has been found that by so doing, the diffusion effects inherent in the spiral plating technique can be cancelled out to the point where they are no longer statistically significant.

The periodicity problem associated with the conventional counting method was solved by simply designing the counting grid so that it did not repeat its spatial relation to the deposition grid during each 360° excursion, but at most only on alternate convolutions. More specifically, it was discovered quite unexpectedly that periodicity in the count virtually disappeared when the counting grid diverged at a rate such that it intersected the corresponding portion of the deposition pattern at radially misaligned points except, perhaps, the beginning and the end. The preferred pattern is the one illustrated wherein the grid spiral intersects the deposition spiral precisely five times from the beginning to the end thereof, the latter points being coincident with one another. This works out such that the counting grid intersects the deposition grid 2½ times per revolution and if one divides 2½ into 360, it will be found that the first intersection is 144° from the start, the second 288°, the third 432° or 72° past S, the fourth 216° past S, and the fifth of course, 360° past S again which brings it back into radial alignment with the original O, all of which is shown in FIG. 3.

Figure 3:
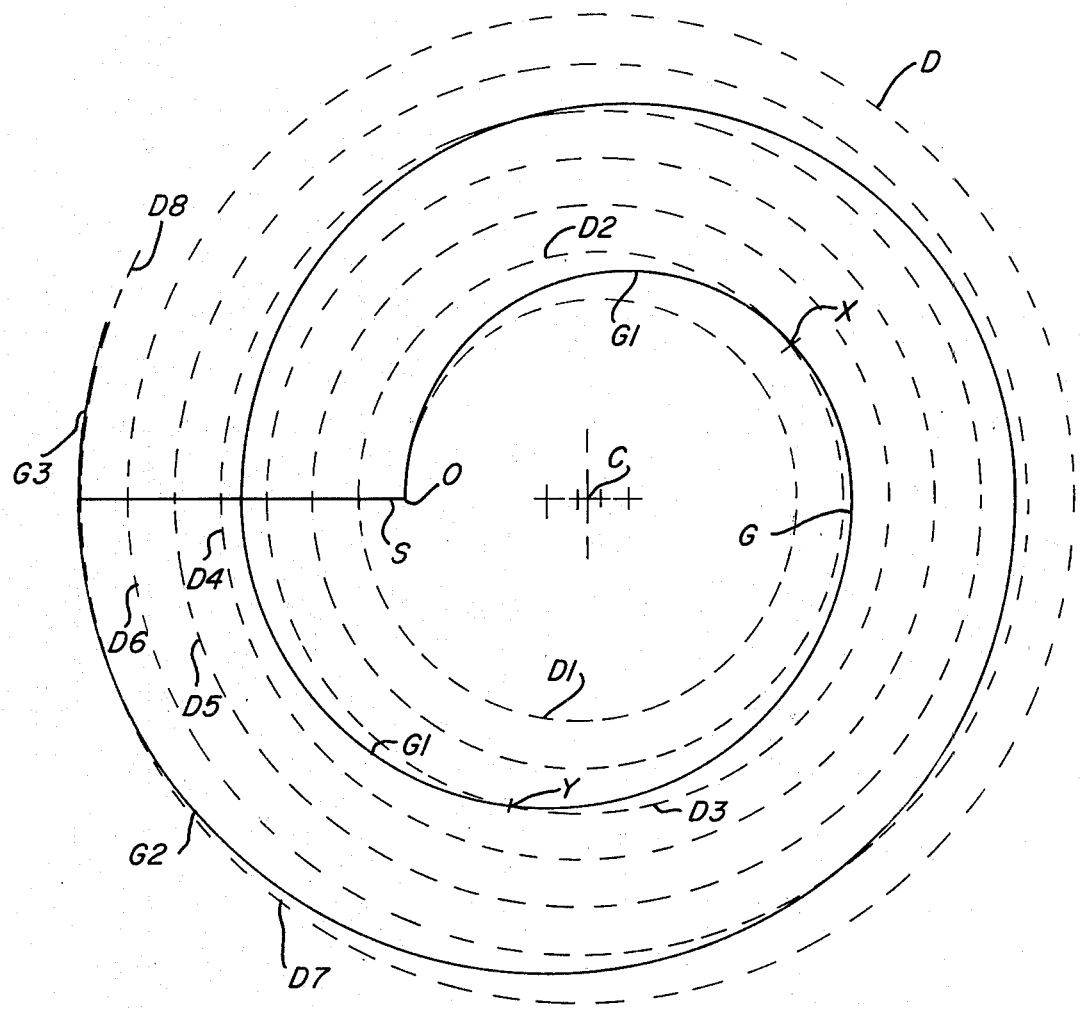

Thus, in accordance with the preferred embodiment shown in FIG. 3, starting at point "0" where both the innermost deposition pattern edge and the innermost counting grid line originate, it will be seen that section G1 of the latter intersects the outer edge D2 of the former at a point X spaced angularly from starting point S precisely 144°. This same innermost counting grid line G1 crosses the outside edge of the second deposition spiral convolution D3 at a point Y 288° from the start S. This, of course, is 72° from the start which means that innermost grid line G1 will only be half way across the space between the inside and outside edges (D3 and D4) of the fourth deposition spiral convolution when it completes one full 360° revolution. Looking at this relationship another way, a given line of the counting grid G intersects an edge of the deposition pattern spiral D exactly 2½ times each revolution. Note also in FIG. 3 that the end of counting grid line G2 and the beginning of counting grid line G3 intersect the outside on edge D8 of the seventh convolution of the deposition spiral at a point in radial alignment with the origin point O. The resultant repetitive relationship between angularly-disposed convolutions of the counting and deposition pattern results in an intersecting pattern has, as previously noted, proven effective in eliminating the periodicity which was experienced with the Ames test when using the prior art concentric circle grid. Having thus devised a grid capable of eliminating, or at least controlling to a statistically insignificant degree, the problems of the prior art grid having to do with diffusion and periodicity. There remained, however, the very significant problem of how to make the cell colony count with sufficient accuracy to provide the data needed for a smooth dose-response curve, two different solutions to this problem having been found, the first of which has been shown in FIG. 1 to which detailed reference will next be made.

Arranged in diametrical relation to the start S of the counting grid G is a wedge-shaped sector W bounded by radii cooperating to subtend an angle of 90°. In the particular form shown, the sector extends 45° on either side of the diameter containing the start S and end E of the counting grid spiral. The grid spiral, of course, includes five convolutions which is the case along any radius. It should be noted, however, that by placing the sector W opposite the start and end of the grid as opposed to the same side thereof, all segments of the spiral convolutions go all the way from one side of the sector to the other. Obviously, this same condition can be found anywhere on the grid except where the radius containing the start and end thereof is located somewhere within the sector W which would result in one foreshortened segment either at the beginning or at the end.

In the particular form shown, sector W is divided into a total of eight counting segments with the two (1 and 2) nearest the center being a full 90° in angular extent while all the remaining ones, 3-8, inclusive, are only 45° in angular extent but two such segments are provided in each convolution of the spiral arranged in end-to-end relation so as to subtend a total of 90°. Segment 2 subtends a greater area than 1, 3 plus 4 a greater area than 2, and so on out to the fifth convolution where segments 7 and 8 have a combined area greater than any of the others. All the divided segments are divided half way so that segments 3 and 4 are equal in angular extent as are 5 and 6 along with 7 and 8. Segment 3 is not, however, equal in area to segment 4, the latter being slightly larger due to its being farther from the center C of the grid. In like manner, starting with segment 3, all higher numbered segments 4 through 8 are larger in area than any preceding one except 2 and 1. The segmented grid just described results in segments which have a decreasing total volume of liquid per segment outward from the center as shown in the following table:

TABLE I

| Volume per segment for FIG. 1 template | |
|---|---|
| Segment # | Total μl/segment |
| 1 | 1.6 |
| 2 | 1.1 |
| 3 | 0.26 |
| 4 | 0.24 |
| 5 | 0.23 |
| 6 | 0.22 |
| 7 | 0.20 |
| 8 | 0.10 |

Each segment, therefore, has a characteristic total volume of liquid and since the basis for a dose-response curve is the fact that the cell colonies must be counted in discrete units of length along the grid spiral so that the number thereof can be related to this known volume and, more particularly, to the concentration of chemical contained within this known volume, segmented grid of FIG. 1 provides the required data in a manner heretofore unknown in the art. The segmented grid shown has no segment under 2 cm in length and this has been found to be quite adequate for purposes of providing the cell count data needed for a good dose-response curve.

Next, looking at FIG. 2, a modified template 10M has been shown which is overlayed by the exact same spiral grid G but which is segmented somewhat differently than the template 10 of FIG. 1. In the former, only a 90° sector of the grid was segmented, whereas, in the latter, all the convolutions of the spiral are segmented beginning at the start S and stopping at the end E. In the FIG. 2 embodiment, however, each of the first fifteen segments is of equal length except for the last or outermost one (16) which is only half as long as the others. There is the further proviso that the segments in adjacent convolutions of the spiral be staggered such that no two, including the first and last, terminate along the same radial line. The first of the sixteen total segments starts at the start of the spiral deposition pattern and continues with all segments from there on being arranged in end-to-end relation. In the actual grid used on a standard 10 cm culture dish, segments 1-15, inclusive, are each 5 cm in length with segment 16 being only 2.5 cm long. This segmented counting pattern results in a decreasing volume of material being deposited from beginning to end that closely approximates that which is shown in the following table:

TABLE II

| Volume per Segment for FIG. 2 template | |
|---|---|
| Segment # | Total μl/segment |
| 1 | 2.7 |
| 2 | 3.0 |
| 3 | 1.9 |
| 4 | 1.5 |
| 5 | 1.3 |
| 6 | 0.98 |
| 7 | 0.95 |
| 8 | 0.74 |
| 9 | 0.66 |
| 10 | 0.49 |
| 11 | 0.42 |
| 12 | 0.42 |
| 13 | 0.38 |
| 14 | 0.32 |
| 15 | 0.27 |
| 16 | 0.10 |

For manual counting, the templates T are inscribed on a transparent material (plastic or glass) which can be illuminated from behind. The culture dishes are placed over the templates and the starting points indicated by the arrows in FIGS. 1 and 2 are aligned. The colonies in each segment are then counted in accordance with techniques well known in the art. The counts are recorded, and then related to the total quantity of chemical deposited in a segment using the known volume in a segment. The cell number is then plotted against concentration of the chemical to obtain a dose-response curve.

What is claimed is:

1. For use in combination with a spirally-deposited solution containing steadily decreasing concentrations of a chemical whose effect upon sensitive bacteria is to be analyzed, the improved means for counting the latter which comprises a transparent underlay imprinted with indicia defining a spiral grid pattern having a beginning point and an end point closely approximating those of the deposition spiral when superimposed thereupon, said grid having at least two convolutions defined in terms of the inner and outer marginal edges thereof and having a clear space therebetween, adjacent convolutions sharing a common marginal edge, the width of the convolutions being constant and spanning at least three convolutions of the deposition spiral, the rate at which said grid convolutions diverge radially from the starting point thereof being greater than the corresponding rate of the deposition spiral such that the convolutions of the former cut across the convolutions of the latter at least twice between the beginning and the end thereof, and at least a portion of the convolutions of said grid spiral being segmented to define a plurality of discrete areas within which the bacteria present can be counted.

2. The counting grid as set forth in claim 1 wherein the width of the counting grid convolutions is approximately three and one-half times that of the convolutions of the deposition spiral.

3. The counting grid as set forth in claim 2 wherein the convolutions of the counting grid intersect the convolutions of the deposition spiral approximately two and one-half times during each revolution.

4. The counting grid as set forth in claim 1 wherein the convolutions of the counting grid intersect the convolutions of the deposition spiral approximately two and one-half times during each revolution.

5. The counting grid as set forth in claim 4 wherein the convolutions of the counting grid intersect the convolutions of the deposition spiral five times between the starting and end points thereof.

6. The counting grid as set forth in claim 1 wherein the starting point and the ending point lie on the same radial line.

7. The counting grid as set forth in claim 1 wherein the convolutions are divided into segments arranged in end-to-end relation.

8. The counting grid as set forth in claim 7 wherein the length of the segments is selected such that no two adjacent segments start on the same radial line.

9. The counting spiral as set forth in claim 8 wherein all adjacent segments both begin and end at different radial points.

10. The counting grid as set forth in claim 7 wherein all the segments except one of the two end segments are of equal length.

11. The counting grid as set forth in claim 10 wherein the end segment is half as long as the others.

12. The counting grid as set forth in claim 1 wherein the counting grid is approximately equal in area to the deposition spiral and shares common starting and end points therewith.

13. The counting grid as set forth in claim 1 wherein the segments are confined to a sector bounded by divergent radii.

14. The counting grid as set forth in claim 13 wherein the sector is approximately 90° in angular extent.

15. The counting grid as set forth in claim 14 wherein the two segments nearest the starting point are 90° in angular extent and all segments outwardly thereof are 45° in angular extent with two such segments being arranged in end-to-end relation within the sector.

* * * * *